Figure 1:
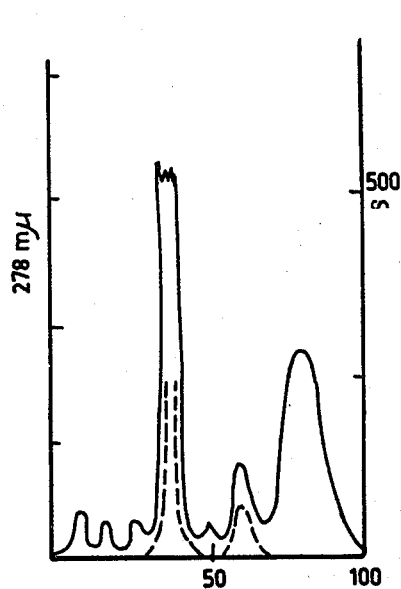

United States Patent [19]

Lucotte et al.

[11] 4,340,591

[45] Jul. 20, 1982

[54] PROCESS FOR OBTENTION OF THE OVOMUCOID FRACTION AND AN OVOMUCOID EXTRACT OF QUAIL EGG, PRODUCTS SO OBTAINED AND THEIR USE AS A MEDICAMENT

[75] Inventors: Gérard Lucotte, Le Fete par Arnay-le-Duc; Jérôme Talamon, Paris, both of France

[73] Assignee: Societe Coturnix, Paris, France

[21] Appl. No.: 147,125

[22] Filed: May 6, 1980

[30] Foreign Application Priority Data

May 7, 1979 [FR] France ................................ 79 11523

[51] Int. Cl.$^3$ ............................................. A61K 37/00
[52] U.S. Cl. ................................ 424/177; 260/112 R; 424/105
[58] Field of Search .................... 424/95, 105, 177; 260/112

[56] References Cited

U.S. PATENT DOCUMENTS 4,112,074  9/1978  Truffier ............................... 424/105

FOREIGN PATENT DOCUMENTS 2356426  1/1978  France .

OTHER PUBLICATIONS

Davis et al.—Biochemistry, vol. 10, No. 1 (1971) pp. 39–42.
Lapuk—Chem. Abst., vol. 66 (1967) p. 43779r.
Chatterjee et al.—Chem. Abst., vol. 58 (1963) p. 5924c.
Truffier et al.—Chem. Abst., vol. 88 (1978) p. 110518z.

Primary Examiner—Sam Rosen
Attorney, Agent, or Firm—Oblon, Fisher, Spivak, McClelland & Maier

[57] ABSTRACT

Obtaining quail egg extracts.

The ovomucoid fraction is obtained by the process consisting in:
(1) adding trichloroacetic acid in solution in acetone to quail egg white;
(2) separating the supernatent from the reaction medium;
(3) adding acetone to the supernatent so obtained;
(4) dissolving the precipitate obtained in step (3) in water and in dialyzing the solution obtained against water;
(5) filtering the resulting solution through a membrane having a cut-off of about 10,000
(6) then subjecting the filtered solution to molecular filtration and in recovering all the fractions having antitrypsin activity.

Application in the treatment of allergic states.

15 Claims, 6 Drawing Figures

PROCESS FOR OBTENTION OF THE OVOMUCOID FRACTION AND AN OVOMUCOID EXTRACT OF QUAIL EGG, PRODUCTS SO OBTAINED AND THEIR USE AS A MEDICAMENT

The present invention relates to a process for obtaining the ovomucoid fraction of quail egg. Its object is also a procedure for obtaining an ovomucoid extract from quail egg and its application as a medicament. It also relates to pharmaceutical compositions containing, as the active principle, the ovomucoid fraction or ovomucoid extract of quail egg.

The therapeutic virtues of quail egg, notably of species *Coturnix coturnix japonica*, for the treatment of asthma and other affections, are recognized in traditional pharmacopoeia in eastern European countries, more particularly in Poland and the Soviet Union. In this connection, reference may be made to Gatewoj's article (Pticew. 5,14, 1968) which reports the results of research conducted under the auspices of the Soviet Institute of Food and Polyclinic and of the Ministry of Health; positive results were obtained with quail egg used in the treatment of asthma, anaemia and ulcers.

In France, experimentation of this type was undertaken with substantially the same results ("Therapeutic approach to allergic disease by the use of quail egg" by J. C. Truffier in "LA CLINIQUE", volume 3, no. 2 22 pages 2–4, March 1978). This experimentation, on more than one hundred cases, demonstrated that it was possible to use quail egg white to treat recurring cases of allergy, asthma, chronic bronchitis, rhinitis and eczema.

French Pat. No. 76 19 751 relates to an ovomucoid fraction of quail egg white having antiprotease properties and a process for obtaining same.

The process described in this French Pat. No. 76 19 751 for obtaining this ovomucoid fraction consists:

(1) in adding a solution of trichloroacetic acid in acetone to quail egg white;

(2) in precipitating the antiprotease fraction by the addition of acetone to the supernatent obtained in step (1);

(3) in dissolving the precipitate so obtained in water, in then effecting a further precipitation with acetone following dialysis against water; and finally (4) in washing and drying the precipitate so obtained.

The ovomucoid fraction so obtained consists essentially of a post-ovalbumin and a protein corresponding to protein Y, this composition having been determined by the proteinogram of said fraction by electrophoresis on starch gel.

Electrophoresis of this ovomucoid fraction, effected on a cellulose column according to the conventional method described by Flodin and J. Porath, Biochim. Biophys. Acta 13 (1954) 175, demonstrated that this ovomucoid fraction actually consisted of 7 fractions, two of which had antitrypsin activity. Electrophoresis was conducted on a column consisting of a 35 mm diameter, 600 mm long "Pyrex" column filled with cellulose to a height of 500 mm; the buffer used was a 0.1 M acetate buffer pH=6,0; electrophoresis was conducted for 42 hours under 160 volts. The resulting elution curve is given in FIG. 1 of the appended drawings, on which the optical density at 278 nm (on the left) and on the other hand the antitrypsin units (on the right) are given as ordinates, and the fractions obtained are given on the axis of the abscissa. The continuous curve is the optical density at 278 nm and the dotted line represents antitrypsin activity in units per fraction.

Simple determinations also showed that the ovomucoid fraction obtained according to French Pat. No. 76 19 751 contained proteins other than ovomucoid:

Spectrofluorometric determination of binding capacity with riboflavin, according to Lucotte and Kaminski's method (Journal of Heredity, 68,201–202, 1977) showed that this fraction contained a preovalbumin.

*The Micrococcus Lysodeikticus* test (Lucotte and Kaminski Biochemical Systematics and Ecology Vol 6, p. 145–147 1978) showed that this fraction contained lysozyme.

The capacity to inhibit the growth of *Saccharomyces cerevisiae* (Lucotte and Kaminski Theorical and applied genetics 48,261–253, 1976) showed that this fraction also contained conalbumin.

Therefore, the process of French Pat. No. 76 19 751 does not permit a purified ovomucoid fraction to be obtained. Such an impure fraction is not suited to human administration. Injected as it stands this fraction can be extremely toxic and dangerous owing to protein shock.

A new procedure for the extraction of quail egg ovomucoid has now been found, making it possible to obtain a pure ovomucoid fraction consisting essentially of ovomucoid.

The process of the invention comprises the following step consisting:

(1) in adding a solution of trichloroacetic acid in acetone to quail egg white;

(2) in separating the supernatent from the reaction medium;

(3) in adding acetone to the supernatent so obtained;

(4) in dissolving the precipitate obtained in step (3) in water and in dialyzing the solution obtained against water;

(5) in filtering the resulting solution through a membrane having a cut-off of about 10,000;

(6) in then subjecting the filtered solution to molecular filtration and in recovering all the fractions having antitrypsin activity.

The first step of the process of the invention is advantageously carried out at a temperature in the range of about 2° to 10° C., and preferably at about 4° C. The addition of a solution of trichloroacetic acid in acetone should be effected slowly and with stirring. 1 volume of 0.5 M trichloroacetic acid for 2 volumes of acetone is generally used.

Then, the reaction medium is left to decant until a clear supernatant is obtained. The supernatant is then separated from the solid fraction.

Acetone is then added to the supernatent obtained at a rate of 1 to 2 volumes per volume of supernatent. The precipitate obtained by the addition of acetone to the supernatent is then dissolved in water.

The resulting aqueous solution is dialyzed against distilled water optionally containing a phosphate buffer; for this purpose, for example, a 0.05 M phosphate buffer pH=7.40±0.05 KCl, EDTA $10^{-3}$, can be used.

The dialyzed solution is then filtered on a membrane having a cut-off of about 10,000 i.e. one retaining substances having a molecular weight greater than about 10,000 and allowing substances with a molecular weight lower than about 10,000 to pass.

This step is a desalting step. For this filtration, for example, a "Diaflo Amicon" cell provided with a PM-10 membrane may be used.

The recovered fraction is then treated by filtration on gel, for example on Sephadex G-50, consisting of a dextrane gel.

All the fractions having antitrypsin activity are recovered. In practice, the various fractions are recovered and each of them is measured for the amount of protein at 280 nm and for antitrypsin activity.

According to the invention, some 600 mg of ovomucoid is obtained for each 100 cm$^3$ egg white.

The fraction so obtained has a single ring in immunoelectrophoresis and immunodiffusion against a specific antiovomucoid antiserum.

The molecular weight of the obtained fraction, assessed in a denaturing medium by the Weber and Osborn method (1969, J Biol. Chem. 244 4406–4412), is in the order of 28,000.

The various determinations effected on the ovomucoid fraction obtained gave the following results:

DETERMINATION OF GLUCIDES (a) hexoses, by the Lusting and Langer method 1931 Biochem. Z. 242, 320–337 with sulphuric orcinol; an amount of 16.4% was determined (b) hexose-amines and osamines: these were previously released by acid hydrolysis in 4 N HCl at 110° C. then determined by the BOAS method [(1953) J. Biol. Chem. 204, 553–563]; 17.8% hexose amines and osamines were found.

(c) sialic acids: Bohm and Baumeister method [(1955) Z. Physiol. Chem. 300, 153–156], using a N-acetyl-neuraminic acid standard, gave a value of 2.9%.

DETERMINATION OF AMINO ACIDS (a) by spectroscopic determination by the Edelhoch method [(1967), Biochem 6, 1948–1954]; the ovomucoid fraction obtained by the process of the invention was found to contain no tryptophan.

(b) The determination of cystines and semi-cystines by determination with the cysteic acid analyzer after performic oxidation, and the determination of carboxymethylcystine residues formed after alkylation with iodoacetic acid of the fraction reduced by mercaptoethanol and denatured with urea and by titration with DTMB showed that the ovomucoid fraction obtained by the process of the invention contained 9 disulphide bridges.

The terminal N of this fraction, determined by 2,4-dinitrofluorobenzine, is a valine.

It is known that quail ovomucoid has antitrypsin activity in humans, antitrypsin activity in bovines and that it does not inhibit bovine chymotrypsin [R. Fenney et al. The Journal of Biological Chemistry, p. 1957–1960, (1969)].

It was confirmed that the fraction obtained by the process of the invention actually had an anti-trypsin activity in humans, anti-trypsin activity in bovines and had no bovine anti-chymotrypsin activity.

Figure 3:
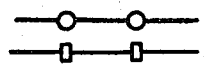
Figure 3:
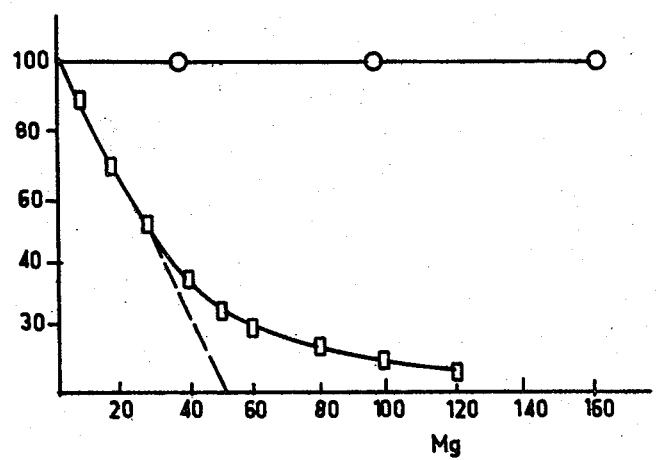

Inhibition of chymotrypsin and bovine trypsin with the ovomucoid fraction obtained according to the invention is shown in FIG. 3, which gives the amount of ovomucoid fraction used in abscissa and the percentage of inhibition for 100 μg of chymotrypsin or trypsin are given as ordinates.

Determination was effected by spectrophotometry at 395 nm by measurement of the acid liberated during the hydrolysis of substrates esterified by trypsin and chymotrypsin. The bovine trypsin or chymotrypsin solution was 50 μg/ml in 0.004 M acetic acid containing 0.02 M $CaCl_2$; the ovomucoid fraction solution was 20 μg/ml in 0.006 M tris buffer pH=8.6; the indicator solution for trypsin was the methyl ester of 0.01 M p-toluene sulfonyl arginine in 0.006 M of tris buffer with 0.02% m-nitrophenol pH=8.2. The indicator solution for chymotrypsin was 0.01 M ethyl ester of benzoyl-L-trypsin in a tris buffer containing 30% methanol and 0.02% m-nitrophenol pH=8.2.

The antitrypsin unit was defined by taking crystallized trypsin as standard: one antitrypsin unit corresponds to the amount of ovomucoid that lowers the hydrolysis velocity of the substrate by 50% per 50 μg of said trypsin.

The ovomucoid fraction obtained by the process of the invention may be used as a medicament for controlling allergies, and particularly for the treatment of asthma, allergic, rhinitis, sinusitis, chronic bronchitis, eczema, urticaria, prurigo, allergic headaches, emphysemia, etc.

The present invention also relates to an ovomucoid extract, a process for obtaining same and its application as a medicament.

It was found that the ovomucoid fraction obtained according to the invention provides, by acid hydrolysis in the presence of pepsin, a histamine-releasing, protease-inhibiting ovomucoid extract.

The process for obtaining ovomucoid extract according to the invention consists:

(1) in adding a solution of trichloroacetic acid in acetone to quail egg white;

(2) in separating the supernatent from the reaction medium;

(3) in adding acetone to the supernatent so obtained;

(4) in dissolving the precipitate obtained in step (3) in water and in dialyzing the solution obtained against water;

(5) in filtering the resulting solution through a membrane having a cut-off of about 10,000;

(6) in then subjecting the filtered solution to filtration on gel, for example on Sephadex G-300, and in recovering the fractions having anti-trypsin activity, in effecting acid hydrolysis of the fraction obtained in step (5) in the presence of pepsin.

in recovering the ovomucoid extract by filtration on gel, for example on a dextrane gel such as Sephadex G-300, in recovering the first peak, quantitatively the largest, that has antitrypsin activity.

Acid hydrolysis is preferably effected in the presence of dilute hydrochloric acid in an amount sufficient to adjust the pH in an acid medium.

Sulphuric acid can also be used. The temperature of hydrolysis is advantageously in the order of 37° C.

Figure 4:
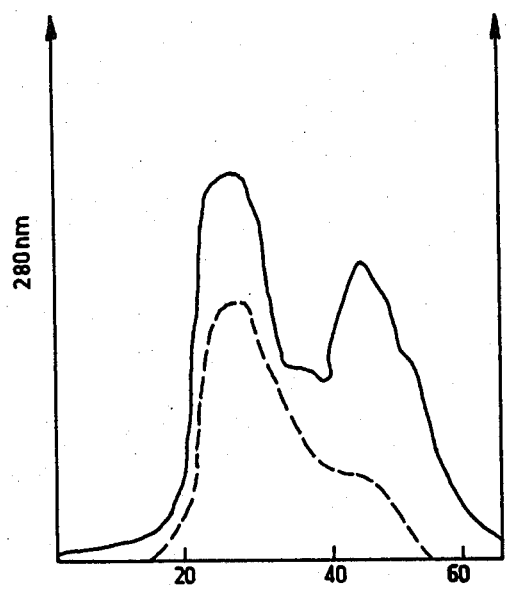

The elution curve obtained is given in FIG. 4 which shows the optical density at 280 nm (ordinates on the left) and human trypsin inhibition in % (ordinates on the right), and the fractions recovered after chromatography are given on the abscissa.

The dissociation constant of the ovomucoid extract of the invention with human trypsin is $2.1 \cdot 10^{-12}$ M. The ovomucoid extract of the invention forms, with the human trypsin, a complex that, for long periods, has an extraordinary resistance to the usual dissociative agents.

The ovomucoid extract of the invention has a molecular weight of about 14,000. The terminal N, determined by the procedure mentioned above in connection with the ovomucoid fraction, is valine. Furthermore, it has 6 disulphide bridges.

It is further characterized by a single ring in immuno-electrophoresis. Moreover, analysis showed that it did not possess tryptophan.

The ovomucoid extract of the invention releases histamine and inhibits protease. It can be used as an active agent to control asthma, allergic rhinitis (pollinosis), allergic sinusitis, chronic bronchitis, eczema, urticaria, prurigo, allergic migraine, emphysemia and Kincke's oedema. It can also be used for hepatitis (cirrhosis), inflammatory states (rheumatism and gout), mucoviscosidosis and pancreatitis.

The invention also relates to pharmaceutical compositions containing, as active agent, the ovomucoid fraction or ovomucoid extract according to the invention.

After volunteers had digested the purified ovomucoid extract or the ovomucoid fraction of the invention, the ovomucoid or its fraction were found to be present in detectable amounts in the patients' blood the day after digestion. This can be proved by immunoelectrophoresis or immunodiffusion using antibodies specific to the purified fractions innoculated to rabbits. The gelose plates then reveal the ring characteristics of the antigen-antibody reaction. The antigenic pattern of the molecule has, therefore, been retained after digestion. The integrity of the molecule is, therefore, maintained. This unexpected property is extremely advantageous as it enables pharmaceutical compositions containing products of the invention to be used by the oral route. This fact is all the more surprising when it is remembered that it is generally agreed that all proteins ingested are destroyed by proteolytic enzymes at the digestive barrier.

The pharmaceutical compositions of the invention can take the form of compositions for administration per os or by injection. In the pharmaceutical compositions, a vehicle is used that is suited to the form of administration chosen, that is pharmaceutically acceptable and inert with regard to the ovomucoid extract. The invention will now be described in greater detail by the following examples purely by way of illustration and in no limitative sense.

EXAMPLE 1

Production of the ovomucoid fraction 600 mg of egg white was used. 1 vol. of a solution of 0.5 M trichloroacetic acid (TCA) in acetone (1 volume of TCA to 2 volumes of acetone) was added to the egg white.

The resulting reaction medium was centrifuged and the supernatant was recovered and precipitated with 2 volumes of acetone. The precipitate was then dissolved in water and the resulting fraction was dialyzed against a 0.05 M phosphate buffer, pH=7.40±0.05 KCl, EDTA $10^{-3}$, the resulting fraction then being concentrated in a "DIAFLO AMICON" cell provided with a PM-10 membrane.

The concentrated fraction was then subjected to chromatography on a SEPHADEX G 50 gel column equilibrated with the beforesaid buffer and the fractions having antitrypsin activity were eluted.

Figure 2:
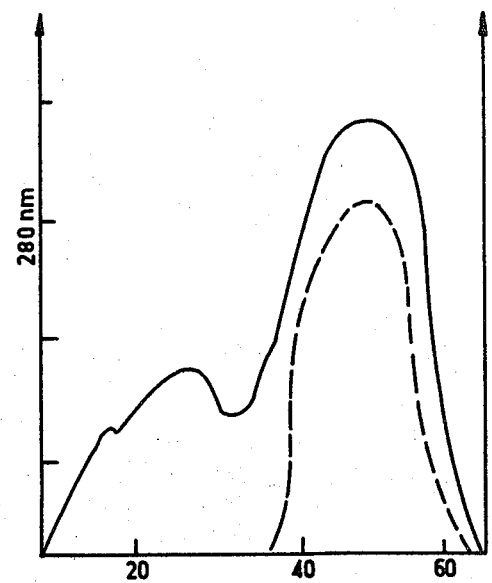

The elution curve of this fraction is shown in FIG. 2 showing, in ordinates, the optical density at 280 nm (on the left) and human antitrypsin activity (on the right) and the number of tubes of the collector containing recovered fractions is given as abscissa.

In FIG. 2, the continuous line represents the level of proteins in the tubes of the collector and the dotted line represents the antitrypsin activity in these tubes. Each tube contained 1.2 ml of liquid.

EXAMPLE 2

The fraction obtained according to example 1 is subjected to acid hydrolysis in the presence of pepsin.

Hydrolysis was conducted for 1 hour at 37° C. with 0.032 N hydrochloric acid in an amount sufficient to obtain a pH of 1.5 in the presence of 0.01% pig pepsin. The fractions having antitrypsin activity were recovered after filtration on Sephadex G-300. The elution curve of the product obtained by hydrolysis is shown in FIG. 4.

In FIG. 4, as was the case in FIG. 2, the ordinates represent the optical density at 280 nm on the left and the antitrypsin activity on the right, and the number of collector tubes is given on the abscissa. Each tube contained 1.5 ml. The continuous line represents the level of proteins and shows a high peak and a low peak. The antitrypsin activity (dotted line) corresponds essentially to the high peak.

Pharmaceutical properties

A—Toxicological Investigation

This was effected in a short term on 100 mice and for four weeks on 10 rats. The accute $LD_{50}$ was 600 to 900 mg/kg, or about 250 times the therapeutic dose.

B—Histamine-Releasing Activity of the Ovomucoid Extract of the Invention.

Intravenous administration of the ovomucoid extract of the invention at a concentration of 15 mg/ml induced a localized pruriginous erythema and a peripheric oedema in the rate. An in vitro biopsy of the subcutaneous conjunctive tissue stained with toluidine blue, and using an optical microscope ($\times 350$) showed that the mastocytes were strongly strained; depositing a solution of the ovomucoid extract at 3 mg/ml concentration induced intense degranulation observable by discharge of granules from mastocytes. Determination of histamine by fluorometry demonstrated releasing of the mediator.

In non-allergic man, intravenous injection of a liminal dose of this ovomucoid extract induced the initiation of anaphylactoid phenomena:generalized tinglings, skin covered with erythema and starting to burn and itch, development of patches of urticaria, increased pulse rate and migraine.

In the case of an allergic subject in a period of remission, an injection of this extract released a system typical of his ailment: for a person subject to urticaria for example, a severe and generalized outbreak of urticaria persisting for several hours was observed; an asthmatic had an attack of asthma. Prolonged, repeated treatment given to the rat, to healthy man and to the allergic subject ended by inducing, by tachyphylaxis, a state of insensitivity of the individual to this extract.

C—Double-blind experimentation

The experimentation was conducted on 160 patients (urticaria, asthma, pollinosis, bronchitis, rhinitis) of both sexes and various ages (men, women, children) who received daily doses of 3 mg ovomucoid extract for two eight-day periods separated by one week without treatment; as the solution was colourless, and absolutely indistinguishable from placebos, the people responsible for administrating it were unaware of the composition of the solutions in the tubes.

The positive results obtained were very markedly better (in the order of 60% cures with adults and 80% in the case of children) to the positive results obtained with placebos, and the signs of the various disorders were observed to disappear progressively.

Clinical silence was, on an average, in the order of 6 months and, in the case of a relapse, a further identical treatment caused all signs of the disorder to disappear.

D—Experimentation on animals

The addition of 3 to 5 mg of the ovomucoid extract of the invention per day for two weeks to the drinking water of 20 dogs suffering from induced eczema of allergic origin resulted in most cases in the cutaneous signs diminishing in a few days and, finally, disappearing.

E—Mechanisms of action and indications (a) Supplementation of protease inhibitor.

Since Laureu and Erikson's publication (Scand. Clin. Lab. Invest. 15, 132, 1963) it has been known that individuals with an $\alpha_1$ antitrypsin deficiency are predisposed to emphysema. In human populations, certain variants of the $\pi$ system are, either in the homozygote form, or in the heterozygote form, deficient in inhibitor, or have markedly low anti-enzyme levels. In addition, it is known (Gerbeaux etal., La nouvelle Presse Medic. 43,3045–50, 1975; Laurell et al., Acta Pediatr. Scand. 63,855–857, 1974; Lieberman, New York State J. Med. USA ,2,181–186, 1976) that individuals with low alpha$_1$ antitrypsin serum levels are predisposed to chronic bronchitis and to asthma (Katz et al. J. Allergy Clin. Immunol. 57, 41, 1976; Arnaud et al. Clin. Res. 244,488, 1978; Scislicki et al., Gruzlica Chor. Pluc. Polska 43,10,929–935, 1975) and particularly to non-allergic infantile asthma.

Figure 5A:
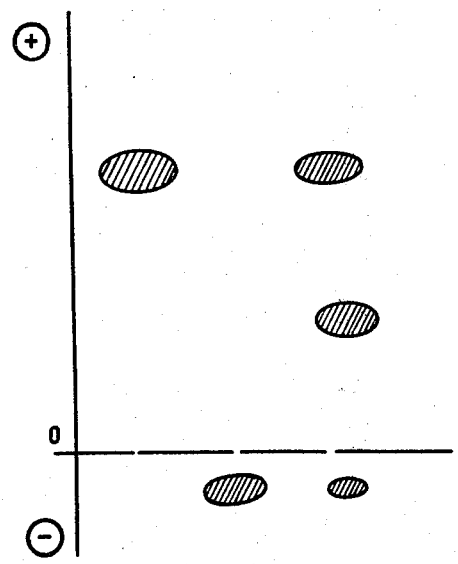
Figure 5B:
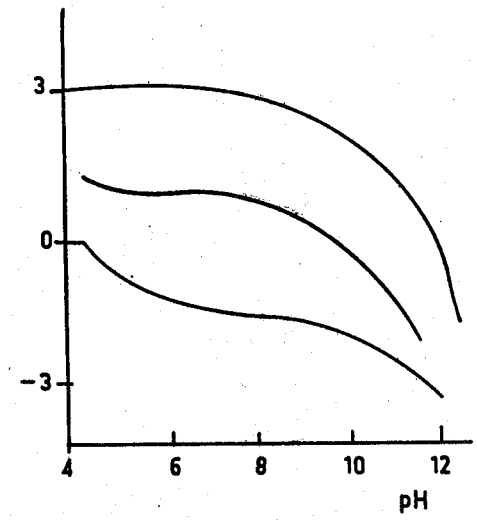

In both these cases, the ovomucoid extract of the invention fulfills a function to provide genetically predisposed individuals with additional trypsin inhibitors that their heredity has not provided them with. FIGS. 5a and 5b give the speed of the electrophoretic migration of the ovomucoid extract of the invention, of human trypsin and of the ovomucoid extract/trypsin complex in starch gel and in pH gradient.

FIG. 5a represents the mobility of the ovomucoid extract of the invention (1), of human trypsin (2) and of the extract/trypsin complex (3) in starch gel (pH=8.6 in discontinuous buffer system and in 2 M urea gel revealed by black amide). FIG. 5b represents the mobility of trypsin, of the ovomucoid extract and of the extract/trypsin complex in pH gradient.

In this type of mode of action, the stability of the complex may be responsible for the long term remission of symptoms. The dose of ovomucoid extract administered per day of treatment is in the order to 3 mg/kg.

This same type of mechanism may also act on the level of the complement. It is known that the $C_3$ and $C_5$ components of the complement can be split, giving $C_{3a}$ and $C_{5a}$ fractions which are anaphylatoxins; now, trypsin (Bokisch et al. J. Exp. Med. 129,1109 1969; Budzko et al. Biochemistry 10, 7, 1971) is an activator of these fractions. This results in individuals suffering from antitrypsin deficiency producing increased amounts of anaphylatoxins [it has already been indicated that asthmatics have a $C_3$ deposit on the bronchial mucus (Covlet et al. Rev. Fr. mal. Resp. 6, 55–60, 1978)] and that in this case also the supplementation of trypsin inhibitor may palliate the production of anaphylatoxins.

(b) immune tolerance

It is known that proteases, and particularly trypsin, adhere to the surface of lymphocytes and change their electrophoretic mobility (Bona et al., Clin. Exp. Immunol. 12,377–390, 1972) and their migration properties (Berney et al., Immunology, 18, 681–691, 1970); furthermore, (Vischer J. Immunol. 113, 58, 1974) trypsin induces blastic transformation of B lymphocytes, but not of T lymphocytes.

The ovomucoid extract of the invention adheres to human lymphocytes. The lymphocytes are obtained by venous fraction and gradient density centrifugation by the FICOLL-HYPAQUE system (Boyum, Scan. J. Clin. Lab. Invest.21, 31, 1968) and cultured in EAGLE(GIBCO) minimum essential medium at a concentration in the order of $10^6$ cells/ml. The mitogenic agent used is Con A(Pharmacia) and the concentration=50 $\mu$g/ml, the transformed and untransformed lymphocytes were observed in the presence of the large ovomucoid fraction after three days incubation, and the detection of the fraction on the surface of the lymphocytes is effected by immunofluorescence observed with an optical microscope. It has been demonstrated that, under these conditions, the ovomucoid fraction does not adhere to human lymphocytes stimulated by Con A; it can therefore participate in the control or proteolytic activity on the surface of the cell membrane, and particularly during blastogenesis.

Injection of the ovomucoid extract (from 25 to 100 $\mu$g) to rats sensitized to ovalbumin induces a marked decrease or, in certain cases, the suppression of the production of IgE specific anti-ovalbumin (determined by Rast) in the presence of this allergen. Inhibition depends on the dose, the IgE production obtained depending on the concentration of the ovomucoid fraction used. This effect has been found in vitro by adding the fraction to a culture of the animal's spleen cells, and it has been shown by washing that the suppression was not directly due to the antigen; however, its presence is indirectly responsible for the production of specific IgE.

This important result shows that the ovomucoid extract of the invention administered in vivo and in vitro to the rat acts as suppressor of the immune response.

What we claim is:

1. A process for obtaining the ovomucoid fraction of quail egg which comprises;
   (1) adding trichloroacetic acid in solution in acetone to quail egg white;
   (2) separating the supernatant from the reaction medium;
   (3) adding acetone to the supernatant so obtained;
   (4) dissolving the precipitate obtained in step (3) in water and dialyzing the solution obtained against water;
   (5) filtering the resulting solution through a membrane having a cut-off of about 10,000;
   (6) then subjecting the filtered solution to chromatographic separation and recovering all the fractions having antitrypsin activity;
   (7) effecting an acid hydrolysis of the fraction obtained in step (6), in the presence of pepsin; and
   (8) recovering the fraction that has antitrypsin activity by filtration on gel.

2. The process according to claim 1, wherein step (1) of the process is effected at a temperature in the range of between about 2° and 10° C., and wherein about 1 volume of trichloroacetic acid for 2 volumes of acetone is used.

3. The process according to claim 2, wherein step (1) of the process is effected at a temperature of about 4° C.

4. The process according to claim 2, wherein the dialysis of step (4) is effected against distilled water containing a phosphate buffer.

5. The process according to claim 4, wherein the chromatographic separation of step (6) is effected on a dextrane gel.

6. The process according to claim 5, wherein the dextrane gel is G-50 Sephadex gel.

7. The process according to claim 1, wherein dilute hydrochloric acid is used for the acid hydrolysis at a temperature of about 37° C.

8. An ovomucoid extract obtained by the process according to claim 1 or 7.

9. An anti-allergenic composition comprising an anti-allergenic effective amount of the ovomucoid extract according to claim 8 in admixture with a pharmaceutically acceptable diluent or carrier.

10. A method for the treatment of allergic states comprising injection of an anti-allergenic composition according to claim 9.

11. A method for the treatment of allergic states comprising oral administration of an anti-allergenic composition according to claim 9.

12. A quail egg ovomucoid extract, characterized in that it has a molecular weight of about 14,000, its terminal N is valine, and in that it has a single ring in immunoelectrophoresis and possesses no tryptophan.

13. An anti-allergenic composition comprising an anti-allergenic effective amount of the quail egg ovomucoid extract according to claim 12 in admixture with a pharmaceutically acceptable diluent or carrier.

14. A method for the treatment of allergic states comprising injection of an anti-allergenic composition according to claim 13.

15. A method for the treatment of allergic states comprising oral administration of an anti-allergenic composition according to claim 13.

* * * * *